United States Patent [19]
Sirna

[11] Patent Number: 5,908,827
[45] Date of Patent: Jun. 1, 1999

[54] PROTEIN FROM URINE NAMED COMPONENT B

[75] Inventor: Antonino Sirna, Rome, Italy

[73] Assignee: Applied Research Systems ARS Holding N.V., Curacao, Netherlands

[21] Appl. No.: 08/448,561

[22] PCT Filed: Dec. 21, 1993

[86] PCT No.: PCT/EP93/03645

§ 371 Date: Jan. 22, 1996

§ 102(e) Date: Jan. 22, 1996

[87] PCT Pub. No.: WO94/14959

PCT Pub. Date: Jul. 7, 1994

[30]   Foreign Application Priority Data

Dec. 22, 1992  [IT]  Italy ................................ RM92A0919

[51] Int. Cl.[6] .................................................. A61K 38/00
[52] U.S. Cl. .................. 514/12; 435/320.1; 435/69.1; 435/252.3; 435/254.11; 435/254.2; 536/23.1; 536/23.5; 536/24.31; 530/412
[58] Field of Search ............................. 514/12; 536/23.1, 536/23.5, 24.31; 435/240.2, 252.3, 254.11, 240.4, 254.2, 69.1, 320.1; 530/412

[56]   References Cited

U.S. PATENT DOCUMENTS 5,298,604   3/1994   Sloane ...................................... 530/351

FOREIGN PATENT DOCUMENTS 0 069 232 A3   1/1983   European Pat. Off. .
82 04261   12/1982   WIPO .

OTHER PUBLICATIONS

Accession No. R3O17 Cohen et al. (1993) Standard Protein; 131 AA.
Accession No. Q2719O Lee et al. (1991) Standard cDNA; 1414 BP.
Accession No. Q1O572 Chang M. et al. (1991) Standard DNA; 1047 BP.
Sloane et al. (1986) Biochem. J., 234:355–362.
R. Ridge et al, "Partial N–Terminal Amino Acid Sequence of the Anti–Neoplastic Urinary Protein (ANUP) and the Anti–Tumor Effect of the N–Terminal Nonapeptide of the Unique Cytokine Present in Human Granulocytes", Cytokine, vol. 8, No. 1 (Jan.), 1996 pp. 1–5.
N. Sloane et al, "Studies on an Antineoplastic Fraction from Human Urine", Biochem. J. (1986) 234, pp. 355–362.
Clinica Chimica Acta, vol. 207 (1992), pp. 239–249. A. Bernard et al., "Human Urinary protein 1: Evidence for identity with Clara cell protein and occurence in respiratory tract and urogenital secretions."

*Primary Examiner*—Rebecca E. Prouty
*Assistant Examiner*—Enrique D. Longton
*Attorney, Agent, or Firm*—Browdy and Neimark

[57]   ABSTRACT

A new protein is described obtainable from urine through an extraction and purification process by ion-exchange chromatography and high resolution chromatography.

15 Claims, 12 Drawing Sheets

FIG. 2A

```
                                          ATG GCC TCT CGC TGG GCT    595
                                          Met Ala Ser Arg Trp Ala
                                          -22         -20
      p
      v
      u
      2
GTG CAG CTG CTG CTC GTG GCA GCC TGG AGC ATG GGC TGT G GTGAGTGGGC    645
Val Gln Leu Leu Leu Val Ala Ala Trp Ser Met Gly Cys
    -15             -10             -5
                                                  S
                                                  T
                                                  Y
                                                  1

CGCAGGCTGG TGGGGACCTT GCCTCTGAGC TTGTCTGCCC ACCTCCTAGG GGGATGGGGC    705
                                    M    S
                                    S    T
                                    T    U
                                    2    1

TGTTGGGGGT GCTTTGTGGC TGAGAGCCTC CTTAGGCCTC CATGAGGCTC ACCCTCCTCA    765
                               B
                               A
                               N
                               2

TTCTCAGTGA GCCTCCTGGG TCCCAGAGCC CAGCTTCACC CTGGGACAGG GGTCACGGCT    825
        P                                                      E
        S                                                      S
        T                                                      P
        1                                                      1

CCACTCTGCA GGAAGGGAGA CTGAGGCTTG GTGGAGGGAT GCAGCATTCA AGTCTGTGGC    885
                                                   A  S
                                                   V  M
                                                   A  A
                                                   1  1

TCAGCTCAGT TAGAGAAAGC TGCCAGAGAG GCCCCTTGAA GGSCTGCCCG GGGCCTTGAA    945
AGATGTCAGC GAGACTCCTT CAGCCCCTGC CTCCTGGTTC CAGGATGAGV CCACCGAGGT   1005
CAGGTGATGA GGTTCTGCCC CCATCCCTCA CCCAG GT GAG GCC CTC AAG TGC       1057
                                           Gly Glu Ala Leu Lys Cys
                                           -3                    1
```

TAC ACC TGC AAG GAG CCC ATG ACC AGT GCT TCC TGC AGG ACC ATT ACC   1105
Tyr Thr Cys Lys Glu Pro Met Thr Ser Ala Ser Cys Arg Thr Ile Thr
     5                   10                  15

CGC TGC AAG CCA GAG GAC ACA GCC TGC ATG ACC ACG CTG GTG ACG GTG   1153
Arg Cys Lys Pro Glu Asp Thr Ala Cys Met Thr Thr Leu Val Thr Val
 20                  25                  30                  35

GAG GCA  G GTGAGGCCAG GCCCCACGGC AGCCCTGGGT GCAGTGGAGT CAGGGCCACC  1210
Glu Ala

TCCCCCAAGT GCGTCCCTCC TTTGCTGGTG CTCCTCCCGG CCCAAAAGGA AGCAGGTGGG  1270
                          S
                          T
                          Y
                          1

ATGGGCAGAA CAGGCTGCCA CACCTTGGCA GGGGTGCCTT CCACGAGGGT GGCACAGCCC  1330

CCTCAGAGAC CCAGTCCTGG GGCACCAGGC GCTGGAGGTG GGTGGGGCTT AATGGCCGGG  1390
           K         B
           P         A
           N         N
           1         2

GTACCCTGGG GGGCTCAAAC CCCAGCTCTG ACACAGACCC ACTGGGTGGT GTTGCCACAG  1450
              AB     B                                       S
              VA     A                                       T
              AN     N                                       U
              12     2                                       1

CCTCTGGGCT CGGGCTCCCA TCTCAGCGCA GGCACTTCAG AGGTCTGACA AGGCCTAATA  1509
                                    B
                                    A
                                    N
                                    2

ATTCATGAAC AGGTCACAGT CAGAGGAGGG CTGGGCCCTG GGTGGCTTCA CAGATGTGGA  1570

CTATTGGGAA CAGGGATCAC AGGGAGGKTG AGGTCAGSCG ACGGCGGCTG GGAGCAGTGC  1630
```

FIG. 2C

```
                P                                                        P
                S                                                        S
                T                                                        T
                1                                                        1
                2
AGCAGCAGGC  AGGCGCTGCA  GGGGAGTGAG  GGTTCTGACA  CTGGCCCACC  CTGCAG  AG  1688
                                                                        Glu

B           B
                            A           S
                            N           T
                            2           E
TAC  CCC  TTC  AAC  CAG  AGC  CCC  GTG  GTG  ACC  CGC  TCC  TGC  TCC  AGC  TCC  1736
Tyr  Pro  Phe  Asn  Gln  Ser  Pro  Val  Val  Thr  Arg  Ser  Cys  Ser  Ser  Ser
     40                       45                      50

B
             A
             L
             1
TGT  GTG  GCC  ACC  GAC  CCC  GAC  AGC  ATC  GGG  GCC  GCC  CAC  CTG  ATC  TTC  1784
Cys  Val  Ala  Thr  Asp  Pro  Asp  Ser  Ile  Gly  Ala  Ala  His  Leu  Ile  Phe
55                       60                      65                         70

TGC  TGC  TTC  CGA  GAC  CTC  TGC  AAC  TCG  GAA  CTC  TGAACCCAGG  GCGGCAGGGC  1837
Cys  Cys  Phe  Arg  Asp  Leu  Cys  Asn  Ser  Glu  Leu
                    75                      80

M
                  S
                  T
                  2
GGAAGGTGCT  CCTCAGGCAC  CTCCTCTCTG  ACGGGGCCTG  GCTCCACCTG  TGATCACCTC  1897

CCCCTGCTTC  CTGCTGCTGT  GGCACAGCTC  ACTCATGGGG  TCTGAGGGGA  GAGAAGCACA  1957

N
        A
        R
        1
CCAGGGGCGC  CCTCTGCCTT  CCATACCCCA  CGCTTATAAA  ACATAACTAA  GCCAAGCGTG  2017

GACATGACTT  TTGT                                                        2031
```

FIG. 3

```
                      E box    E box                                         E box
           TGGCCCATGC TACCCTCACC TGACACCTGC TTCCTACCTC TGGTTTCTAC TTTGCAGGTG   60
              E box
           TGTATCAGGT GTACACAGAC CAGGTAGAGG TCTGTGGAGA GGGCTGCAGG CCAGGCTGCA  120
           GGGAAGGGGT GCCAGGCGGG GCTAGAGCAA CAAGGGCAGA GGCTACACTG AACCTGGGTC  180
                           AP-2
           YTAAGGGTCC CCCAGGCTGG GGCTGGGTGG CCTATGTGAA CCCCAGAGGC ACAGCCAGGA  240
           CATGGGGGCT CATCAGAGGG GCAGTCTGAG CTCAGCAGGA AAGGCCTTCT CTGTCAGAGC  300
                                            GRE
           TGTCCCAGGA CCACTGGACA TGGCTGAGGA ACAGTGAGTT CCCCAGTGTT GGAGGTGTGC  360
           AAGCAGAGGC CTGGCCATCG TCCTCAGACA CAGCTCCCAG ATCCAGCTCC CTGCCCGTCT  420
                           E box                                AP-1
           GCCATGTTCC TGCCAGCTGC CTCCCCACTG GGCCCTTTAC CACGTTCCTG ACTCACACGG  480
                         Sp-1                              TATA box
           CCGGTTCTGC CACCGCCCAG AAGCCGGTGC CCAAGGGCCT GGCTATAAAT CCTTGATGTG  540
           AGGCTGGCTA CCTCTCATCA CTTCTGAGCA CGGAGCA
```

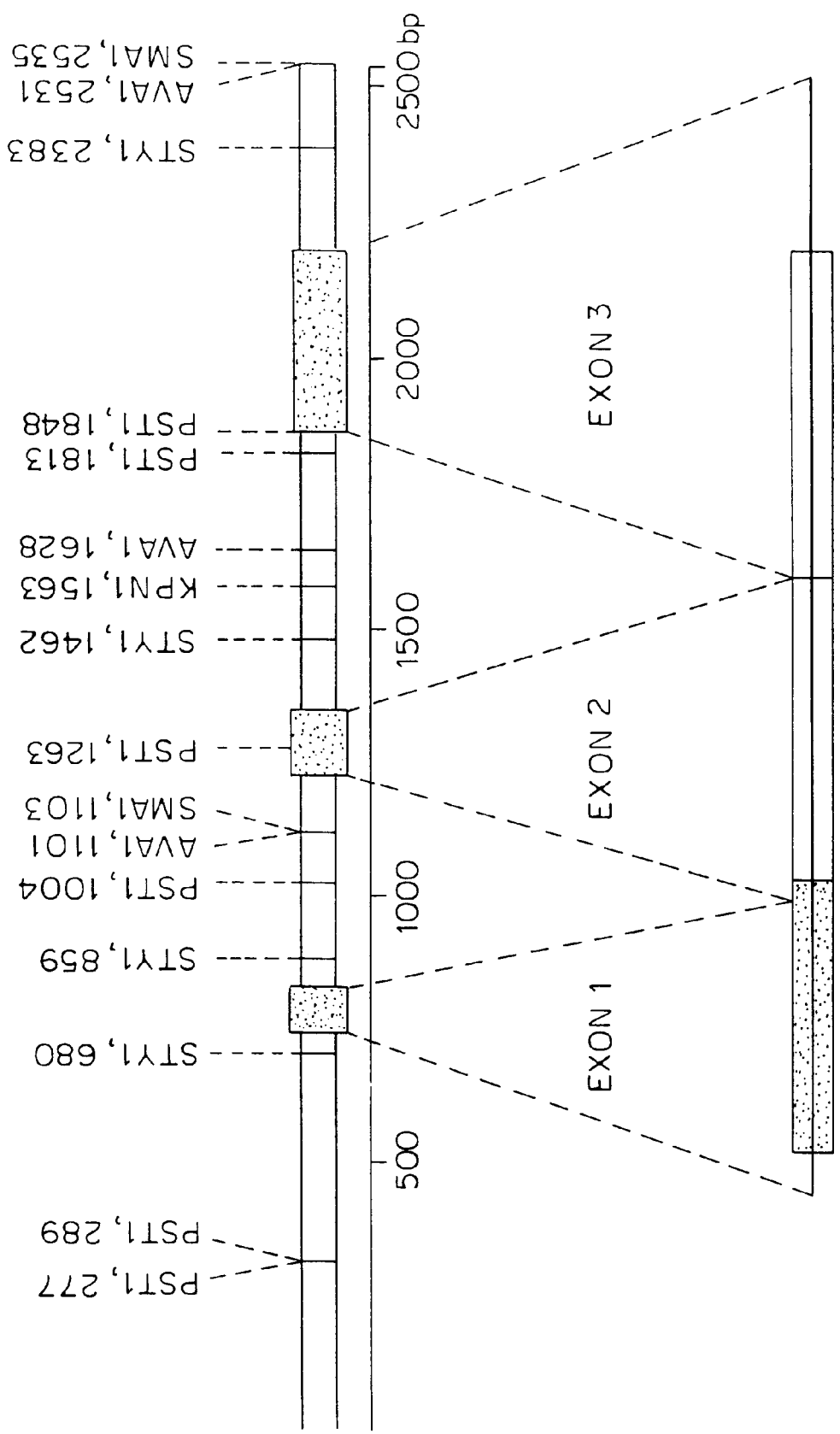

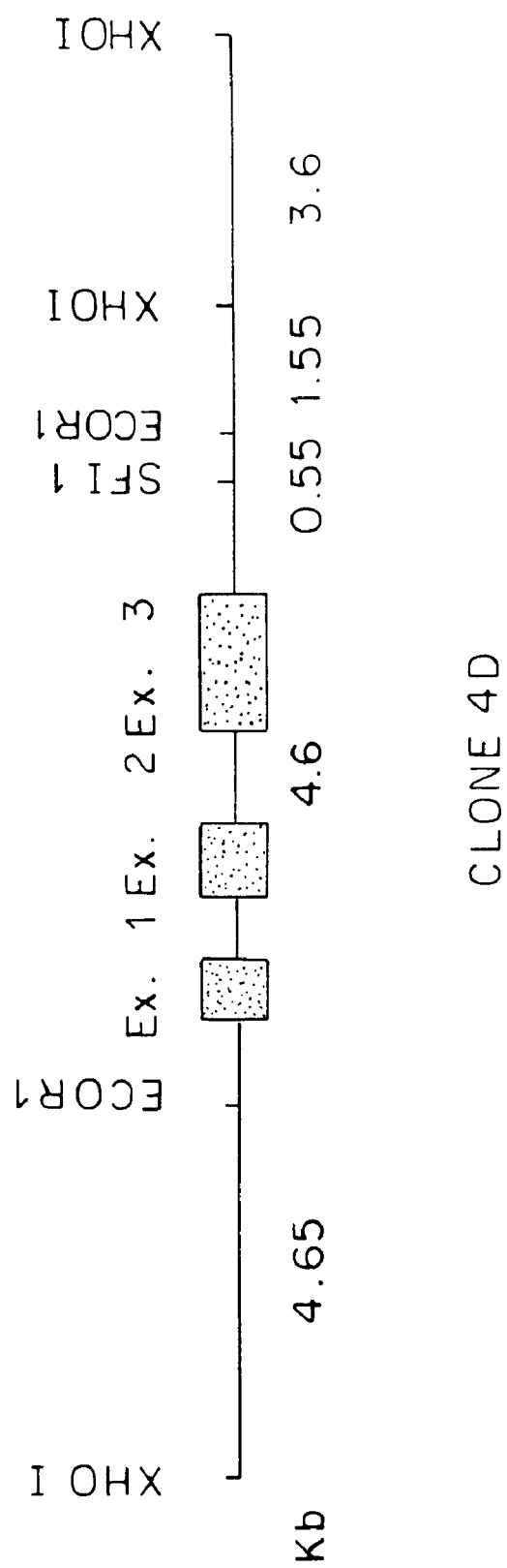

FIG. 8A

```
                       B
                       s
                       As                                                    N
                       11          B                                         sP   AA
                       w2          Hs                                        pv   lp
                       28          ar                                        Bu   wa
                       16          eD                                        II   NB
                       II          II                                        II   II
                        /                                                     /
ATCACTTCTG AGCACGGAGC A ATG GCC TCT CGC TGG GCT GTG CAG CTG CTG              51
                       Met Ala Ser Arg Trp Ala Val Gln Leu Leu
                       -22     -20                     -15
```

```
                                              E
                                              c
                              B               o
                              c               0
              B               e               B1
              s               8               p0
              g               3               m9
              I               I               II
                                               /
CTC GTG GCA GCC TGG AGC ATG GGC TGT GGT GAG GCC CTC AAG TGC TAC              99
Leu Val Ala Ala Trp Ser Met Gly Cys Gly Glu Ala Leu Lys Cys Tyr
        -10                     -5                   1
```

```
                      B                             S
                      s                             s
                      p                             e                  N
              B       B1                            8                  s
              s       a2                    S       P3                 p
              p       n8                    f       s8                 B
              M       I6                    c       t7                 I
              I       II                    I       II                 I
                       /                             /
ACC TGC AAG GAG CCC ATG ACC AGT GCT TCC TGC AGG ACC ATT ACC CGC              147
Thr Cys Lys Glu Pro Met Thr Ser Ala Ser Cys Arg Thr Ile Thr Arg
  5              10                15                   20
```

```
                                        M
                                        s
                                        l
                                        I
TGC AAG CCA GAG GAC ACA GCC TGC ATG ACC ACG CTG GTG ACG GTG GAG              195
Cys Lys Pro Glu Asp Thr Ala Cys Met Thr Thr Leu Val Thr Val Glu
              25                  30                  35
```

FIG. 8B

```
                            B
                            s
                            p         B
                         B1 s         B
                         a2D  Bt      s
                         n8s  pE      r
                         I6a  mI      B
                         III  II      I
                          //   /
GCA GAG TAC CCC TTC AAC CAG AGC CCC GTG GTG ACC CGC TCC TGC TCC    243
Ala Glu Tyr Pro Phe Asn Gln Ser Pro Val Val Thr Arg Ser Cys Ser
            40                  45                  50

A
    1X          E   HM
    wc          a   as
    Nm          e   ec
    II          I   II
                     /
AGC TCC TGT GTG GCC ACC GAC CCC GAC AGC ATC GGG GCC GCC CAC CTG    291
Ser Ser Cys Val Ala Thr Asp Pro Asp Ser Ile Gly Ala Ala His Leu
        55                  60                  65

B       B                                       B
        c       s                                       c
        g       a                                       g
        I       I                                       I
ATC TTC TGC TGC TTC CGA GAC CTC TGC AAC TCG GAA CTC TGAACCCAGG     340
Ile Phe Cys Cys Phe Arg Asp Leu Cys Asn Ser Glu Leu
    70                  75                  80

B                       E
                        s                       c
                    A   p B                     o
                    1   1Bs                     0
         B          w   2su   B                 1
         sE         2   8e3   a                 0
         ec         1   6R6   n                 9
         Ri         I   III   I                 I
          /              / /
GCGGCAGGGC GGAAGGTGCT CCTCAGGCAC CTCCTCTCTG ACGGGGCCTG GCTCCACCTG  400

B
c
l
I
TGATCACCTC CCCCTGCTTC CTGCTGCTGT GGCACAGCTC ACTCATGGGG TCTGAGGGGA  460
```

FIG. 8C

```
         B   H
       BsN   a
       aaa   e
       nHr   I
       III   I
         /
GAGAAGCACA CCAGGGGCGC CCTCTGCCTT CCATACCCCA CGCTTATAAA ACATAACTAA  520

GCCAAAAAAA AAAAAAAAA                                                540
```

… # PROTEIN FROM URINE NAMED COMPONENT B

This is a national stage application of PCT/EP93/03645 filed Dec. 21, 1993 and claims benefit to Italian application number RM92A00919 filed Dec. 22, 1992.

FIELD OF THE INVENTION

The present invention relates to a new protein named Component B. In particular the invention relates to a new protein obtainable from urine, its preparation from urine, its production by recombinant DNA techniques using genomic DNA or cDNA encoding said new protein, as well as pharmaceutical compositions containing it and its use in therapy.

SUMMARY OF THE INVENTION

A new protein was isolated during the extraction and purification process of urine derivatives. This protein shows a polypeptide nature and relatively low molecular weight. When human urine is treated with adsorbing materials, as kaolin, and then undergoes filtration, ion exchange chromatography and high resolution chromatography, preferably according to the process hereafter described, after lyophilisation a compound is obtained as amorphous white powder, moving as an a single peak in high pressure reversed phase liquid chromatography (HPLC-RP) and having a molecular weight of about 9 KDa when analysed by electrophoresis on a polyacrylamide gel in the presence of sodium dodecyl sulphate (SDS-Page) under reducing conditions. This protein was named, and is referred to hereinafter as, Component B.

Component B is more specifically characterised through the amino acid sequence reported as SEQ ID NO: 1.

The present invention makes therefore available a new protein, named Component B, obtainable through a process comprising the isolation of a raw fraction of the compound itself from a dialysed concentrate of urine after treatment with an adsorbing agent and its purification by ion exchange chromatography and high resolution chromatography as described hereafter.

Preferably the protein according to the present invention is extracted from human urine because of the high amount available. This technique is thus useful for industrial production. The present invention refers particularly to a polypeptide comprising the SEQ ID NO: 1, its salts, functional derivatives, precursors and active fractions as well as its active mutants, i.e. other proteins or polypeptides wherein one or more amino acids of the structure were eliminated or substituted by other amino acids or one or more amino acids were added to that sequence in order to obtain polypeptides or proteins having the same activity of Component B and comprises also the corresponding fusion proteins i.e. polypeptides comprising Component B or a mutation thereof fused with another protein and having a longer lasting half-life in body fluids. Component B can therefore be fused with another protein such as, for example, an immunoglobulin.

The definition "salts" as used herein refers both to salts of the carboxyl-groups and to the salts of the amino functions of the compound obtainable through known methods.

The salts of the carboxyl-groups comprise inorganic salts as, for example, sodium, potassium, calcium salts and salts with organic bases such as those formed with an amine as triethanolamine, arginine or lysine. The salts of the amino groups comprise, for example salts with inorganic acids such as hydrochloric acid and with organic acids such as acetic acid. The definition "functional derivatives" as herein used refers to derivatives which can be prepared from the functional groups present on the lateral chains of the amino acid moieties or on the terminal N- or C-groups according to known methods and are comprised in the invention when they are pharmacetically acceptable i.e. when they do not destroy the protein activity or do not impart toxicity to the pharmaceutical compositions containing them.

Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

The "precursors" are compounds which are converted into the Component B in the human or animal body. As "active fractions" of the protein the present invention refers to any fragment or precursor of the polypeptidic chain of the compound itself, alone or in combination with related molecules or residues bound to it, for example residues of sugars or phosphates, or aggregates of the polypeptide molecule when such fragments or precursors show the same activity of Component B as a medicament.

The present invention refers also to a mixture of polypeptides and derivatives as said above.

A second aspect of the present invention concerns the process of preparation or Component B, such process comprising the isolation of a raw fraction or the protein from a dialysed concentrate of urine after treatment with an adsorbing agent and its purification through ion exchange chromatography and high resolution chromatography.

Preferably, Component B is prepared through the process illustrated in FIG. 1 and comprising the following steps:

a) adsorption of urine at acid pH on kaolin and extraction with ammonia
b) elution of fraction (a) on Bio Rex 70 resin with ammonia
c) elution of fraction (b) on DEAE Sepharose resin with acetate buffer
d) elution of fraction (c) on CM Sepharose ion exchange resin with acetate buffer
e) elution of fraction (d) on HPLC C18 ion exchange resin with a mixture of acetate buffer and acetonitrile
f) elution of fraction (e) on DE-52 ion exchange resin with acetate buffer
g) elution of fraction (f) on D-Zephyr ion exchange resin with acetate buffer
h) elution of fraction (g) on HPLC C18 ion exchange resin with a mixture of aqueous trifluoroacetic acid and acetonitrile
i) elution of fraction (h) on D- Zephyr ion exchange resin with acetate buffer.

The present invention refers also to recombinant DNA molecules which comprise the nucleotidic sequence encoding the polypeptide according to the invention, its active mutants or fusion proteins, expression vectors which comprise it, host-cells transformed with such vectors and a process of preparation of such polypeptide, its active mutants or fusion proteins, through the culture in appropriate culture media of said transformed cells. The definition "recombinant DNA molecules" include genomic DNA, cDNA, synthetic DNA and combinations thereof. In particular the present invention refers to the nucleotide sequences illustrated in SEQ ID NO: 2 and SEQ ID NO: 3 respectively.

SEQ ID NO: 2: reports the genomic DNA sequence encoding Component B; FIG. 2 reports the restriction map of Component B transcriptional unit;

SEQ ID NO: 3: reports the cDNA sequence encoding Component B; FIG. 8 shows the complete Component B cDNA sequence, in which the restriction sites are indicated. The cloning of Component B can be performed through different techniques. According to one of these techniques an oligonucleotide, or a mixture of oligonucleotides, are prepared, their sequence being derived from the sequence of Component B or its fragment and used as probe for cloning the cDNA or the genomic DNA encoding Component B.

SEQ ID NO: 4: reports the amino acids sequence encoded both by the genomic DNA reported in SEQ ID NO: 2 and by the cDNA reported in SEQ ID NO: 3.

The present invention also refers to recombinant DNA molecules which hybridize with the DNA sequence coding for Component B or fragments thereof.

The gene can contain, optionally, the natural introns and can be obtained for example by extraction from appropriate cells and purification with known methods. Appropriate preparations of DNA, as human genomic DNA, are cut in the appropriate way, preferably with restriction enzymes, find the so obtained fragments are introduced in appropriate recombinant vectors in order to form a DNA library. Such vectors can be selected with synthetic oligonucleotide probes in order to identify a sequence encoding Component B according to the invention.

In particular, according to the present invention, the genomic DNA of Component B was isolated and cloned.

On the other hand, the corresponding mRNA can be isolated from the cells expressing Component B and used to produce the complementary DNA (cDNA) with known methods. This cDNA after having been converted in the double helix, can be introduced in an appropriate vector which can afterwards be used for transforming an appropriate host cell. The resulting cultures are then selected with an appropriate probe in order to obtain the cDNA encoding the targeted sequences. Once the wanted clone is isolated, the cDNA can be manipulated essentially in the same way as the genomic DNA.

The cDNA does not contain introns.

Because of the degeneration of the genetic code, various codons can be used for encoding a specific amino acid, so that one or more oligonucleotides can be produced, each of them being able to encode fragments of Component B. However only one member of this pool possesses the nucleotide sequence identical to that of the gene. Its presence in the pool and its capacity of hybridizing with the DNA also in the presence of other members of the pool makes it possible the use of the group of non fractioned oligonucleotides in the same way as a single oligonucleotide could be used for cloning the gene encoding the targeted peptide. Alternatively, a single oligonucleotide containing the sequence which is theoretically the most probable for encoding the genetic fragments of Component B (according to what described in the "rules for the use of codons" in Lathe R., et al. J. Molec. Biol. 183:1–12 (1985)) allows the identification the complementary DNA encoding Component B or a fragment thereof.

The processes for hybridizing the nucleic acids are known and described, for example in Maniatis T. et al. Molecular Cloning: A laboratory manual, Cold Spring Harbor Press, Cold Spring Harbor, N.Y., 1982) and in Haymes B. T. et al. Nucleic Acid Hybridization: A practical approach, IRL Press, Oxford, England. (1985). Through the hybridization using said probe or group of nucleotide probes it is possible to identify in a genomic or cDNA gene library the DNA sequences capable of such hybridization which are thereafter analysed to confirm that they encode the polypeptide according to the invention (i.e. Component B). The oligonucleotide which contains such complementary sequence can be synthetized and used as a probe to identify and isolate the gene of the polypeptide according to the invention i.e. Component B (Maniatis T. et al. ibid.).

Once the appropriate oligonucleotide specific for Component B is selected using the above said method, it is possible to synthetize and hybridize it with a DNA, or preferably with a cDNA derived from cells capable of expressing the wanted gene preferably after the source of cDNA was enriched of wanted sequences, for example by extraction of the RNA from cells producing high levels of the wanted gene and conversion of the RNA into the corresponding cDNA using the enzyme reverse transcriptase.

Alternatively, the suitable oligonucleotides specific for Component B can be synthesised and used as primers for the amplification of Component B cDNA fragments by RACE-PCR (M. A. Innis et al., PCR Protocols, A Guide to Methods and Applications, Academic Press, 1990).

In particular, according to the present invention, a screening of different human and cellular tissues was performed firstly in order to identify the best available source for mRNA of Component B. Human tissues from brain, kidney, liver, lung, heart, pancreas, placenta, spleen, testis, thymus and uterus as well as epitheliod carcinoma, promyelocytic leukemia, breast adenocarcinoma, Burkitt's lymphoma and myeloma cell lines were screened for this purpose.

The screening was performed by using a sensible assay "reverse transcriptase—polymerase chain reaction" (RT-PCR).

Human uterine tissue provided the best source of mRNA.

The cDNA clones of Component B were obtained by said tissue using the amplification method named "3' and 5' rapid Amplification of cDNA Ends" (RACE).

The DNA molecules encoding Component B, obtained with the above said method, were introduced in expression vectors constructed with known techniques (Maniatis T. et al. ibid.). The double helix cDNA is ligated to plasmid vectors using, for example, techniques comprising the use of synthetic DNA adapters or techniques of binding "blunt-ended".

For the expression of a targeted protein, an expression vector should comprise also specific nucleotide sequences containing the information regulating transcription and translation bound to the DNA encoding the desired protein in such a way that the expression of the gene and the production of the protein are permitted. First of all, in order that the gene can be transcribed, it must be preceded by a promoter which can be recognised by the RNA polymerase and to which the polymerase binds, thus starting the transcription process.

Many promoters are known which operate with different efficiency (strong and weak promoters) which are different if used in prokaryotic or eukaryotic cells.

The promoters which can be used in the present invention can be constitutive, as for example promoter int of lambda bacteriophage, promoter Bla of the gene of β-lactamase of pBR322 and the promoter CAT of the gene of chloramphenicol acetyltransferase of pPR325 ecc., or inducible as for example the promoters of prokaryotes as the main right and left promoters of lambda bacteriophage (Pl and Pr), the promoters trp, rec A, lac Z, lac I, ompF and gal of *E. coli*, or the hybrid promoter trp-lac, etc. (Glik B. R. J. Ind. Microbiol. 1:277–282 (1987).

Together with the strong promoters which are capable of producing huge quantities of mRNA, giving high levels of gene expression in prokaryotic cells, it is necessary to use also binding sites for the ribosomes in order to assure that the mRNA is efficently translated.

An example is given by he Shine-Dalgarno (SD) sequence positioned in appropriate way from the starting codon.

For eukaryotic host cells different sequences regulating the transcription and translation can be used according to the nature of the host.

These can be derived from viral sources, as adenovirus, or papilloma virus, Simian virus or similar, wherein the regulation signals are associated with a specific gene having a high level of expression. Possible examples are the promoter TK of the herpes virus, the promoter of SV40, the promoter of gene gal4 of yeast ecc. The signals regulating the starting of transcription can be suitably chosen in order to produce repression or activation in such a way that the expression of the genes can be accordingly modulated.

The DNA molecule comprising the nucleotide sequence encoding Component B of the invention together with the signals regulating transcription and translation are introduced in a vector which is capable of integrating the sequences of the targeted gene in the host cell chromosome.

The cells which bear the introduced DNA in their chromosome can be selected also introducing one or more markers which make it possible to select the host cells containing the expression vector. The marker can provide the cells, for example, with antibiotic resistance or heavy metal (as copper) resistance. The selection gene can be directly bound to the DNA sequences which must be expressed or can be introduced in the cell itself by cotransfection. Other elements may also be necessary for a higher gene expression. These elements can comprise for example transcription enhancers and termination signals and introns. Expression vectors which include such elements comprise those described by Okayama H. Mol. Cell. Biol. 3:280 (1983).

Among the factors to be considered for chosing a particular plasmid or viral vector are: the facility of detection of the cells containing the vector which can be easily separated from those which do not contain it; the number of copies of vectors which are wanted in a specific host, and the possibility, or not, of transferring the vector among different host cells.

The preferred prokaryotic vectors comprise plasmids as those capable of replication in *E. coli*, as pBR322, ColE1, pSC101, pACYC 184 etc. (Maniatis T. et al, ibid.), Bacillus plasmids as pC194, pC221, pT127 etc. (Gryczan T. M. The Molecular Biology of the Bacilli, Academic press, N.Y., 307–329 (1982) Streptomyces plasmids as pIJ101 (Kendall K. J. et al. J. bacteriol. 169:4177–4183) and Pseudomonas plasmids (John J. F. et al. Rev. Infect. Dis. 8: 693–704 (1986) (Izaki K. Jpn. J. Bacteriol. 3: 729–742).

The preferred eukaryotic vectors comprise, for example, BPV, SV40, Baculovirus etc. or their derivatives. Such vectors are known in the art (Bostein D. et al. Miami Wint Symp. 19: 265–274) (Broach J. R. The Molecular Biology of the Yeast Saccharomyces: Life Cycle and Inheritance, Cold Spring Harbor, N.Y., 455–470 (1981) (Broach J. R. cell 28:203–204 (1982) (Bollon D. P. et al. J. Clin. Hematol. Oncol. 10: 39–48 (1980) (Maniatis T. Cell Biology: A Comprehensive Treatise Vol. 3: Gene Expression Acad. Press N.Y. 563–608 (1980).

The expression vector so prepared is introduced in the appropriate host cell with an appropriate method such as transformation, transfection, lipofection, conjugation, protoplastic fusion, electroporation, precipitation with calcium phosphate, direct microinjection etc. The host cell which can be used for the present invention can be prokaryotic or eukaryotic cells.

Preferred prokaryotes include bacteria such as *E. coli*, Bacillus, streptomyces, pseudomonas, Salmonella, Serratia, etc.

Particularly preferred is *E. coli*, as for example strain 294 of *E. coli* K12 (AtCC 314446) or *E. coli* X1776 (ATCC 31537), *E. coli* W 3110 (F, lambda, ATCC 27325).

Preferred eukariotic host cells are mammalian cells such as human, monkey, mouse or hamster (Chinese Hamster Ovary, CHO) cells since they assure to the protein molecules post-translation modifications, as for example the correct folding and glycosylation in the right positions.

Yeast cells can be also used for the present invention. There are various recombinant DNA techniques which utilize sequences of strong promoters and a high number of copies of the plasmid and allow the production of the wanted protein in yeast.

After the introduction of the vector in the host cells these are cultivated in a medium which allows the selective growth of cells containing the vector.

The expression of the cloned DNA sequence allows the production of Component B, or a mutant or fragment thereof. The so expressed protein is isolated purified through conventional techniques comprising extraction, precipitation, chromatography, electrophoresis, or similar techniques, or affinity chromatography, using anti-Component B antibodies immobilised on the column gel. Component B can also be produced as milk-secreted protein in transgenic animals.

A further aspect of the present invention is the use of Component B, its salts, functional derivatives, precursors or active fractions as a medicament.

In particular Component B has shown anti-inflammatory, anti-coagulant and anti-tumoral properties. Furthermore Component B can be useful in the therapy of pathologies correlated with altered levels of TGF-alpha, such as behavioral and hormonal disturbances, angiogenesys, etc.

In fact, Component B has been shown to inhibit the binding of TGF-alpha to its receptor with an affinity constant is $K_i=0.77 * 10^{-10}$ M measured by displacement of $I^{125}$-TGF-alpha from its receptor, obtained from A 431 cell membranes.

The pharmaceutical compositions containing a therapeutically active quantity of Component B in combination with pharmaceutically acceptable excipients or eluents are also an object of the present invention. Such compositions can be formulated for oral, rectal, nasal and particularly parenteral administration.

Also the topic use of Component B is included in the present invention.

The formulations according to the invention include also forms as subcutaneous implantations based on liposomes or microcapsules of copolymers of lactic and glycolic acids.

Other aspects of the invention will be evident in the light of the following detailed description.

DETAILED DESCRIPTION OF THE INVENTION

EXAMPLE 1

Process of preparation of Component B from human urine

Figure 1:
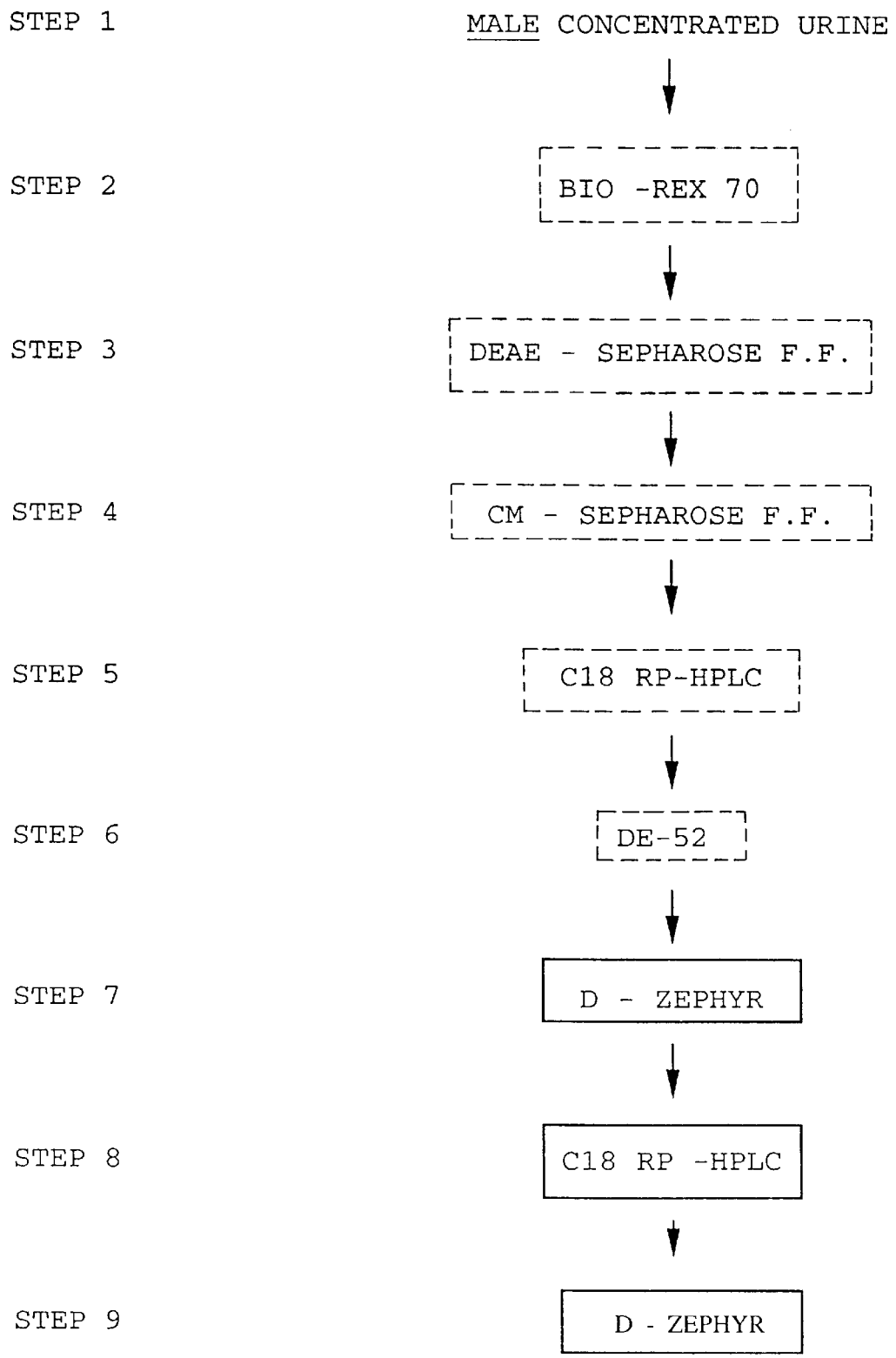

The preparation and purification of Component B from human urine is summarized in FIG. 1.

a) STEP 1

The starting material is human urine to which HCl is added up to pH 3.0. After decantation of the precipitate, kaolin is added to the urine (10 g/l of starting urine).

The suspension is left for 16 hours and is thereafter centrifuged. The supernatant is eliminated and kaolin is extracted with ammonia 2M pH 11.0.

The ammonia eluate pH is brought to 8.0 and is concentrated by membrane ultrafiltration (cut off 1000 Daltons). The whole operation is performed at 4° C.

b) STEP 2

The solution obtained in step (a) is added with acetic acid up to pH 4.0 and then with Bio Rex 70 resin, a weak cation exchange resin, R-COO previously equilibrated at pH 4.0 with acetic buffer.

The solution is left under stirring for 4 hours and is then filtered on a pressfilter.

The adsorbed material is eluted from the Bio Rex 70 resin through elution with ammonia at pH 9.0.

The chromatography eluate is concentrated by membrane ultrafiltration (cut off 1000 Daltons). The whole operation is performed at 4° C.

c) STEP 3

The material obtained in step (b), equilibrated in acetic buffer pH 5,6 is adsorbed on an ion exchange resin like DEAE Sepharose, previously equilibrated at pH 5,6.

At the end of the adsorption elution is performed using ammonium acetate buffer 0.5M at pH 5.6. The chromatography eluate is concentrated by membrane ultracentrifugation (cut off 1000 Daltons). DEAE (diethlaminoethyl) Sepharose is a fast flow weak anion exchange resin. The whole operation is performed at 4° C.

d) STEP 4

The material obtained in step (c) is equilibrated with acetate buffer at pH 4.5 and adsorbed on ion exchange resin like CM (carboxymethyl) Sepharose, a fast flow weak cation exchange resin, previously equilibrated at pH 4.5.

When the adsorption is completed elution is performed with ammonium acetate buffer 0.15M pH 4.5. The chromatography eluate is concentrated by membrane ultrafiltration (cut off 1000 daltons). The whole operation is performed at 4° C.

e) STEP 5

The material obtained in step (d) is purified at 25° C. by reverse phase chromatography on HPLC C18 resin equilibrated in ammonium acetate buffer 0.05M pH 5.6.

The adsorbed material is eluted from the resin with an ammonium acetate solution containing acetonitrile 30% (v/v). The chromatography eluate is concentrated by distillation (40° C.) under vacuum.

f) STEP 6

The material obtain in step (e) is purified on ion exchange resin like DE-52, equilibrated at pH 5.6 in ammonium acetate buffer 0.02M.

The elution of the adsorbed material is performed with buffer 0.25M. The concentration is performed by membrane ultrafiltration (cut off 1000 Daltons). The whole operation is performed at 4° C.

g) STEP 7

The material obtained in step (f) is purified on ion exchange resin like D-Zephyr, a weak anion exchange resin (substituted tertiary amine) prepacked column (sold by Sepracor), equilibrated at pH 6.2 in 20 mM sodium acetate buffer solution (buffer A).

The elution of the absorbed material is performed by gradient elution from 100% buffer A to 100% 20 mM sodium acetate buffer solution at pH 6.2 containing 1M NaCl.

h) STEP 8

The material obtained in step (g) is purified by reversed phase chromatography at 25° C. on resin C18 like HPLC.

After adsorbtion the elution is perfomed with linear gradient formed by a binary mixture of an aqueous solution of trifluoroacetic acid (TFA 0.1%) and acetonitrile, acidified with TFA (0.1%). The chromatography eluate was concentrated by distillation (45° C.) under vacuum and lyophilized.

i) STEP 9

Step 7 is repeated.

The final product, Component B, is recovered as an amorphous white powder.

EXAMPLE 2

Analytical characterisation of component B

In order to specify the main physical-chemical characteristics of Component B the purified material from urine underwent the following analytical controls.

a) AMINO ACID SEQUENCE

The amino acid sequence of Component B was determined according to the Edman method The analysis was Performed using a sequencer Applied Biosystem, model 477A, following the indications given by the producer. Such analysis made it possible to identify the amino acid sequence or component B relatively to the 81 amino acid residues reported in SEQ ID NO: 1.

b) DETERMINATION OF MOLECULAR WEIGHT

The analysis was performed by "Electron Spray—Mass Spectrometry" (ES-MS) and showed a molecular weight of 8937.9 Daltons. Such analysis has shown the presence of five disulfide bridges and an 80 Daltons residue attributable to an $SO_4$ group bound to Tyr (39).

EXAMPLE 3

Isolation of Human Component B genomic DNA

A human genomic DNA library in lambda phage vector EMBL-3 SP6/T7 was purchased from Clontech (cat. No. HL 1067 J, Lot No. 1221). Genomic DNA was extracted from human placenta and partially digested with Sau 3A. DNA fragments were separated on a sucrose gradient to produce a size range between 8 to 22 Kb before cloning into the BamHl site of EMBL-3 Sp6/T7 vector.

Culture media

*E. coli* K802 cells, purchased from Clontech (cat. No. C1004-1), were cultured in LB medium supplemented with 10 mM $MgSO_4$ and 0.2% maltose (culture medium).

The phage library was diluted in 0.1M NaCl, 8 mm $MgSO_4$, 50 mM Tris-Cl pH 7.5, 0.01% gelatin (SM).

The DNA library was plated onto 1.5% agar-LB plates. Top agarose for library plating was: 0.136M NaCl, 0.6% agarose, 1% tryptone (Merck cat No. 7213).

Hybridization reagents

20×SSC 3M NaCl, 0.3M Na citrate, pH 7.0

Hybridization solution 5×SSC, 0.02% SDS, 0.1% N-lauroylsarcosine, 0.5% Blocking reagent (Boehringer cat No. 1096176).

Washing solution A 3×SSC, 0.1% SDS, urea at various concentrations depending on the specific probe (HRP-oligos) (see below).

Washing solution B 1×SSC. 0.1% SDS ($^{32}$P-oligo CBEX4L)

Detection system

HRP-oligo/DNA hybrids were detected by ECL kit and exposure to Hyperfilm ECL from Amersham (cat. No. RPM 2106 and 2104, respectively).

$^{32}$P-oligoprobed filters were developed by exposure to Hyperfilm β-max (Amersham cat. No. RPN10).

Oligonucleotides

Oligonucleotides were synthesized by an automatic DNA synthesizer (Applied Biosystem mod. 392).

Oligonucleotides were purified by OPC cartridges (Applied Biosystem cat. No. 400771) or by denaturing PAGE.

Oligonucleotides CB1, CB2 and CBEX2L to be used as probes were 5' modified with N-MMT-C12-aminomodifier (Clontech cat. No. 5206-1) during the last cycle of synthesis.

Horse-radish peroxidase (HRP, Boehringer cat. No. 814393) was conjugated to the modified oligonucleotide according to M. S. Urdea (Nuc. Ac. Res. 16, 4937, 1988), by using 1,4-phenylendiisothiocyanate (Aldrich cat. No. 25,855-5) as a homobifunctional crosslinking agent.

HRP-oligoprobes were purified by anion-exchange HPLC on a Nucleopac PA-100 column (Dionex cat. No. 043010). Elution was performed with 20 mM Na phosphate buffer pH 6.0 and a linear gradient of NaCl from 0.2 to 1.0M in 30 min..

Purified HRP-oligonucleotides were concentrated by Centricon 10, washed with PBS and stored at 4° C. in the dark. The HRP-oligonucleotide concentration was calculated by $OD_{403}$ ($\epsilon_{403}$=89.5 $cm^{-1}xmM^{-1}$).

The following oligonucleotides were synthesized:

Blotted DNA was then neutralized by placing the filters onto a filter paper soaked in neutralizing solution (1.5M NaCl, 0.5M Tris-Cl pH 7.2, 1 mM EDTA) twice for 3 min each.

Filters were washed in 2×SSC and air-dried. DNA was fixed to the membrane by placing the filters onto a filter paper soaked in 0.4M NaOH for 20 min.

The filters were finally washed in 5×SSC for 1 min and stored in a plastic bag at 4° C. up to hybridization. The human genomic DNA Library (1×10$^6$ clones) was screened at high plating density with HRP-CB2 oligoprobe. 20 positive clones were selected.

Six positive clones were rescreened with both HRP-CB1 and HRP-CB2 oligoprobes. Three clones, named 4D, 12B and 15, were confirmed to be positive for the gene for Component B.

Hybridization

Filters were preincubated at 42° C. for 30 min in the hybridization solution, then hybridized with the appropriate HRP-oligoprobe (5 ng/ml oligonucleotide moiety in hybridization solution) at 42° C. for 45 min and finally washed twice for 15 min each at 42° C. in washing solution containing urea at the appropriate concentration (see below).

Filters were washed briefly in 2×SSC at room temperature and the hybridized plaques were detected by ECL reagents and exposure to Hyperfilm for 60 min.

| oligo # | sequence | target | |
|---|---|---|---|
| CBPU1 | 5'TGACTCACACGGCCGGTTCT | promoter | SEQ ID NO: 5 |
| CBPL1 | 5'CAGCCATGTCCAGTGGTCCT | promoter | SEQ ID NO: 6 |
| CBEX2L | 5'ACCACAGCCCATGCTCCA | exon 1 | SEQ ID NO: 7 |
| CB1 | 5'TGCAGGAAGCACTGGTCAT | exon 2 | SEQ ID NO: 8 |
| CB2 | 5'TCTGGCTTGCAGCGGGTAATGGT | exon 2 | SEQ ID NO: 9 |
| CB3 | 5'ATGACCAGTGCTTCCTGC | exon 2 | SEQ ID NO: 10 |
| CB5 | 5'ATCCCACCTGCTGCCTTTTG | intron 2 | SEQ ID NO: 11 |
| CBEX4U2 | 5'CGGCGGCTGGGAGCAGT | intron 2 | SEQ ID NO: 12 |
| CBF1 | 5'ATGGAATTCTAYCCATTYAAYCARTC | exon 3 | SEQ ID NO: 13 |
| CBF2 | 5'ATGGAATTCTAYCCATTYAAYCARAG | exon 3 | SEQ ID NO: 14 |
| CBR1 | 5'GTAGAATTCGCGCCAATGGARTCNGGRTC | exon 3 | SEQ ID NO: 15 |
| CBR2 | 5'GTAGAATTCGCGCCAATGCTRTCNGGRTC | exon 3 | SEQ ID NO: 16 |
| CBEX4U | 5'AGTACCCCTTCAACCAGAG | exon 3 | SEQ ID NO: 17 |
| CBEX4L | 5'CAGACACCATGAGTGAGCTG | exon 3 | SEQ ID NO: 18 |
| CBEX4U1 | 5'GACACCTCCTCTGTGACGG | exon 3 | SEQ ID NO: 19 |
| CBEX4L1 | 5'CCAGTTCTGTAGGGTGTCAGT | exon 3 | SEQ ID NO: 20 | where R = A-G, Y = C-T and N = A-G-C-T.

Library titration

The human genomic DNA library was titred according to standard procedures (F. Ausubel, Current Protocols in Molecular Biology) by infecting 0.3 ml of an overnight culture of E. coli K802 cells with various dilutions of the library, in the range 2×10$^{-3}$ to 2×10$^{-7}$. Cell-library mixture was incubated at room temperature for 20 min, then transferred to 37° C. for 10 min. Infected cells were mixed with 4 ml of top agarose preheated at 50° C. and poured onto a 10 cm agar plate prewarmed 37° C. Plates were incubated at 37° C. overnight (ON).

The number of plaques was scored in each plate. Duplicate plates were prepared for each library dilution. The human genomic DNA library titer was found to be 5×10$^9$ pfu/ml, as expected.

Library screening

E. coli K802 cells grown overnight at 37° C. 0.6 ml of cell culture were infected with a library aliquot (6×10$^4$ pfu) suspended in SM. Infection and plating was performed as above, but 9 ml of top agarose and 15 cm plates were used.

Semiconfluent plaques were transferred onto Hybond N$^+$ nylon membrane (Amersham), according to Amersham instruction manual. flotted DNA was denaturated by placing the filters, plaque side up, onto a filter paper soaked in 1.5M NaCl, 0.5M NaOH for 7 min.

Washing conditions for HRP-oligoprobed filters were experimentally determined to minimize unspecific hybridization to E. coli and lambda phage DNAs. Serial dilutions in the range 500 to 15 attomoles of target DNA were spotted on Hybond N$^+$ membrane in the presence of lambda DNA (10 ng). Lambda and E. coli DNAs (10 ng each) were used as negative controls. Several strips were prepared and used in hybridization experiments with 5 ng/ml probe. Washings were performed with washing solution A containing 0, 9, 18, 27 and 36% urea.

18% and 27% urea were found effective for CB1 and CB2, respectively. Filters hybridized with CBEX2L were washed with washing solution A containing 18% urea.

Hybridization with $^{32}$P-oligo CBEX4L was performed at 50° C. and filters were washed at 45° C. in washing solution B.

Plaque subscreening

Positive plaques were picked up by a Pasteur pipette and transferred to a tube containing 1 ml of SM plus a drop of chloroform. After 2 hr incubation under shaking at room temperature, the phage suspension was stored at 4° C.

A 10$^{-3}$ dilution of the phage suspension was plated onto a 10 cm plate and rescreened on two replicate filters with two oligoprobes, i.e. the one used in the first screening and another one matching to an adjacent region of component B.

Independent clones positive for both probes were picked up and resuspended as above.

Preparation of phage stocks

Positive clones were expanded by infecting E. coli K802 cells and growing on 15 cm agar plates. After ON incubation at 37° C., the confluent lysate was collected from agar plates with 10 ml of SM. A few drops of chloroform were added, cell debris were removed by centrifugation at 3000 rpm for 5 min at 4° C. and the clear supernatant containing the phages was brought to 50% glycerol, aliquoted and stored at −80° C.

Extraction of phage DNA $2 \times 10^9$ E. coli K802 cells were infected with the selected phage clone (cell/phage ratio=4:1) and grown in 100 ml liquid culture medium ON at 37° C. At the end of incubation, full cell lysis was accomplished by adding chloroform (5 μl/ml) to the culture. Phage DNA was extracted by Quiagen, according to the manufacturer's instructions.

Phage DNA sequencing

Phage DNA was sequenced using a cycle sequencing kit from Applied Biosystem (cat. No. 401388) with an automated DNA sequencer (Applied Biosystem mod. 373A). Phage DNA was extracted from clones 4D, 12B and 15 and sequenced by cycle sequencing.

Sequencing primers were derived either from the amino acid sequence of Component B (CBF1, CBF2, CBR1, CBR2) or from the available cDNA or genomic DNA sequencing data.

Sequencing data indicated that the three clones contained the full-length Component B gene.

Phage DNA restriction analysis

Phage DNA was subjected to single and multiple restriction enzyme digestions. DNA fragments were resolved by 0.6% agarose gel electrophoresis and then blotted onto Hybond N+ membrane. Filters were repeatedly probed with oligonucleotides CBEX2L, CB2 and CBEX4L, matching to exon 1, 2 and 3 respectively.

Subcloning of Component B gene in pBlueScript II SK

Restriction analysis of Component B clone 4D with EcoR1, Xho I and Sfi 1 and Southern blotting with oligoprobes specific for the three exons of Component B indicated that the entire Component B gene was contained in a 5.2 Kb EcoR1 fragment. (FIG. 5).

Phage DNA was extracted from clone 4D and digested with EcoR1. The resulting DNA fragments were resolved by agarose gel electrophoresis. The 5.2 Kb fragment was purified by Qiaex (qiagen cat. No. 20020) and ligated to EcoR1 linearized pBlueSript II KS (Stratagene cat. No. 212207). E. coli strain XL1-Blue (Stratagene cat. No. 200268) was transformed with the ligation mixture and transformed cells were selected on Ap/Tc plates. One clone containing the expected plasmid, as shown by resctriction analysis with EcoR1, was isolated and named pBSCB4D.

Further restriction analysis was performed with Sma1, Kpn1, Hind III, Sfi1, Acc1, Not1, Sal1, Xho1, EcoRV, Cla1, Hinc II, Hind II, Sca11, Bgl II, Aat 2, Nco1, Nhe1, Hpa1 and Mlu1. In addition Southern blotting was performed with Component B specific oligoprobes on pBSCB4D after single and double digestions.

Figure 6:
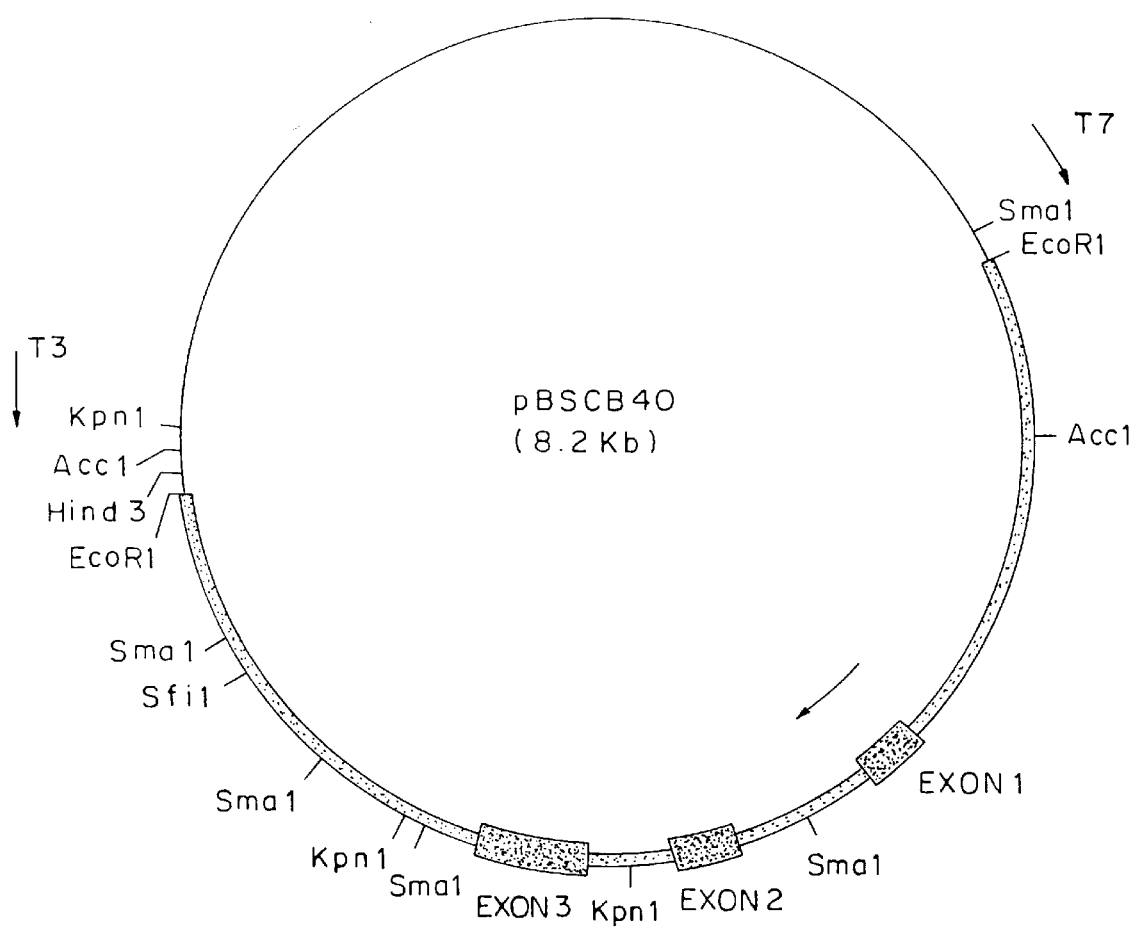

FIG. 6 shows the restriction map of pBSCB4D plasmid.

FIG. 4 shows the restriction map of Component B gene. The Component B gene contains 3 exons separated by 2 introns. The exons are flanked by appropriate consensus acceptor and donor splice sites.

Exon 1 is 84 bp in length and contains 26 nt of untraslated mRNA and the sequence coding for 19 amino acids of a putative signal peptide. It is separated from exon 2 by an intron of 410 bp.

Exon 2 is 120 bp in length and codes for 3 amino acids of a putative signal peptide and 37 amino acids of the mature protein. It is separated from exon 3 by an intron of about 550 bp.

Exon 3 is 326 bp long; it encodes the C-terminal 44 amino acids of Component B and 197 nt of untraslated mRNA, containing a polyadenylation signal (TATAAA) 14 bp upstream to the 3' processing site, to which end the poly(A) tail is attached.

In particular, in the three genomic clones the signal peptide encoding sequence was found to contain a Leu codon at position 11 of the putative signal peptide.

The amino acid sequence of Component B derived from the genomic gene was found to be identical to the one experimentally determined by Edman degradation.

Sequence analysis upstream to exon 1 evidentiated a promoter region (FIG. 3) and corresponding to nucleotides 1-577 of SEQ ID NO: 2) containing a TATA box at -28 and various upstream promoter elements and enhancers, including a GC-rich box at -58, an AP-1 site at -83, an AP-2 site at -360 and several E boxes.

The TATA box is the preferred binding site for the transcription initiation factor TFIID. The GC-rich box represents the binding site for Sp-1, a general transcription factor involved in the transcription of a wide variety of genes (Transcription and Splicing B. D. Hames & D. M. Glover Eds, IRL press, 1988).

The AP-1 site is the binding site for AP-1, the transcription factor complex formed by c-fos and c-jun. The AP-1 site is present in several genes involved in cell growth and differentiation. AP-1 is one of several cis-elements that mediate induction responses to activators of protein kinase C (The hormonal control of gene transcription P. Cohen & J. G. Foulkes Eds. Elsevier, 1991).

The AP-2 site is the target for AP-2, a transcription factor activated by PMA and cAMP (ibidam).

E boxes are common sequences found in several enhancer regions and play an important role in determing the tissue-specific expression of genes. E box contains the sequence CANNTG, with the two internal bases changing according to the specific E box (R. E. Kingston Current Opinion Cell. Biol. 1989; 1, 1081–1087).

The Component B promoter contains a potential responsive element for glucocorticoid receptor (GRE), which indicates that the Component B gene could be induced by glucocorticoids.

Subcloning of Component B gene in a vector for expression in mammalian cells

It is known that the expression of rec-proteins in mammalian cells may be improved by the presence of intron(s). The Component B genomic DNA can be expressed in mammalian cells.

To this end, a 1364 bp fragment spanning Component B gene from +50 to +1413 is excised from pBSCB4D by Pvu II and Nar 1 digestion.

FIG. 2 shows the restriction map of Component B transcriptional unit where Pvu II and Nar1 sites are based. The entire Component B gene is reconstituted by ligation of this fragment with a synthetic oligonucleotide reproducing the 5' end of the gene, flanked by a suitable restriction site for the subsequent gene cloning in an eukaryotic expression plasmid.

Example 4: Isolation of Component B cDNA clones

Figure 7:
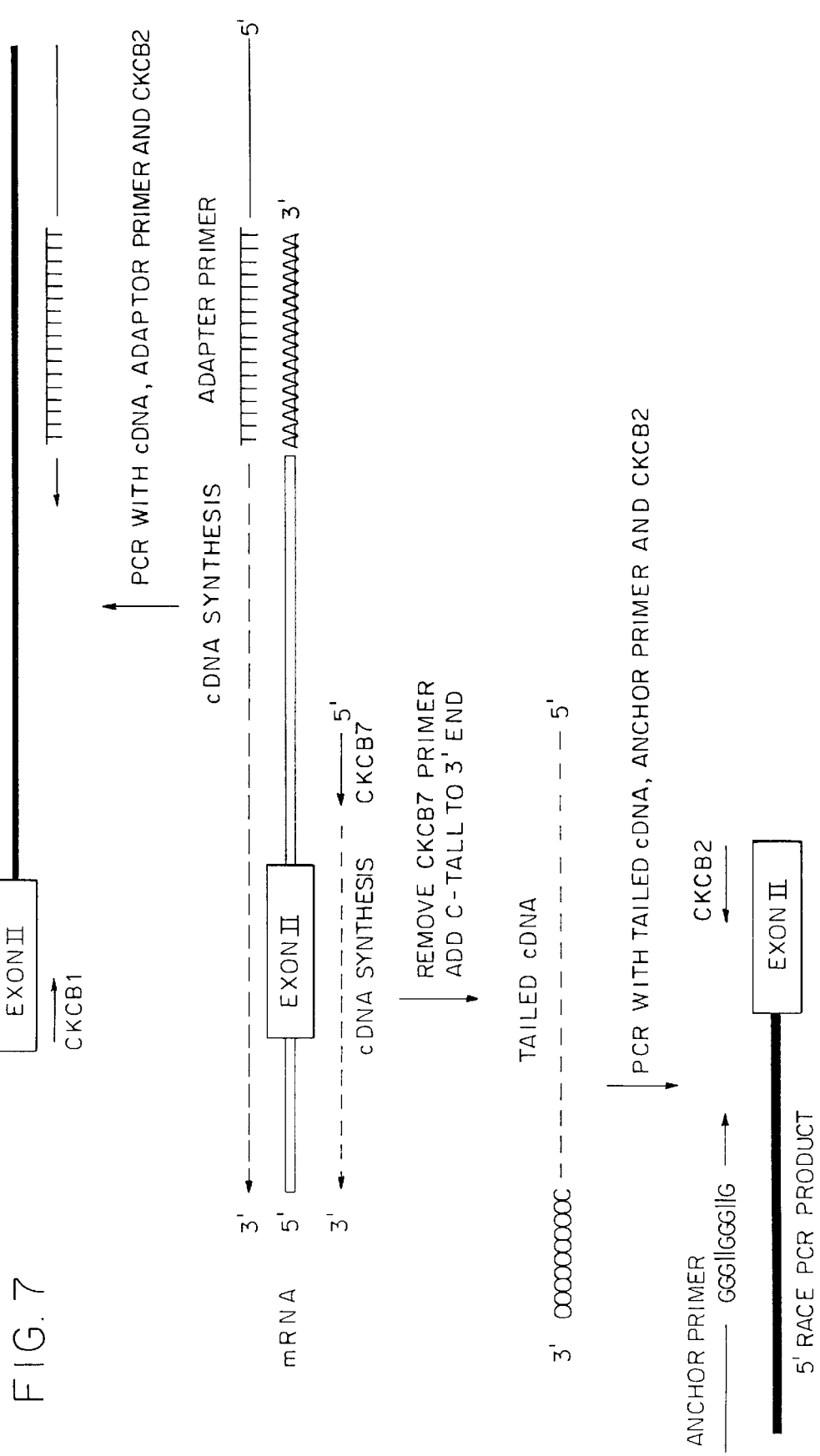

Rapid Amplification of cDNA Ends (RACE), a technique described by Frohman et al., (1988) Proc. Natl. Acad. Sci. U.S.A. 85, 8998, was used to obtain partial cDNA clones corresponding to the 5' and 3' ends of the Component B mRNA. The partial clones contained overlapping DNA sequences and thus could be combined to construct the full-length Component B cDNA sequence. A diagram depicting the general strategy used for RACE cloning is shown in FIG. 7.

For 3' RACE, the DNA sequence of the second exon of the Component B gene was available and was used to design the gene specific primer CKCB1 (5'-TCAAGTGCTACACCTGCAAGGAG-3') (SEQ ID NO: 21). cDNA synthesis was primed from the poly A tail of human uterus poly $A^+$ RNA with the oligonucleotide 5'-GGCCACGCGTCGACTAGTAC-3' (SEQ ID NO: 24), called the adapter primer of AP. The cDNA was used as the template for a polymerase chain reaction (PCR) with the CKCB1 and AP primers, which produced an approximately 450 base pair (bp) fragment corresponding to the 3' end of the Component B cDNA.

For 5' RACE, the primer CKCB7 (5'-CGTCAGAGAGGAGGTG-3') (SEQ ID NO: 22 was designed from the DNA sequence of the 450 bp 3' RACE fragment and was used to prime cDNA synthesis from human uterus poly $A^+$ RNA.

After purification to remove the mRNA and the CKCB7 primer, an oligodeoxycytidine tail was added to the 3' end of the cDNA. The tailed cDNA was used as the template in a PCR with the nested primer CKCB2 (5'-ACCGTCACCAGCGTGGTC-3') (SEQ ID NO: 23) and the anchor primer (ACP, 5'-CTACTACTACTAGGCCAC GCGTCGACTAGTACGGGIIGGGIIGGGIIG-3') (SEQ ID NO: 25) or a mixture of the ACP and the universal amplification primer (UAP, 5'CTACTACTACTAGGCCACG CGTCGACTAGTAC-3') (SEQ ID NO: 26). CKCB2 annealed to the 3' end of the second exon sequence and the ACP annealed to the oligodeoxycytidine tail. An approximately 230 bp fragment was obtained which contained DNA sequence corresponding to the 5' end of the Component B mRNA.

General experimental protocols (such as polyacrylamide gel electrophoresis, ethanol precipitation, ligation, and restriction endonuclease digestion), bacterial culture media (such as LB) and chemical solutions (such as phenol) used are described in detail in Sambrook et al, (1989) Molecular Cloning: A Laboratory Manual, 2nd ed., Cold Spring Harbor Laboratory Press. New York, unless otherwise referenced.
3' RACE cloning procedure The 3' RACE System for Rapid Amplification of cDNA ends was purchased from Life Technologies, Inc., Grand Island, N.Y. Human uterus poly $A^+$ RNA was purchased from Clontech Laboratories, Inc. Palo Alto, Calif. First strand cDNA synthesis was accomplished using the protocol and reagents supplied with the 3' RACE system. Briefly, 1 $\mu l$ (1 $\mu g$) of uterus poly $A^+$ RNA was combined with 1 $\mu l$ of a 10 $\mu M$ solution of AP and 12 $\mu l$ of diethyl pyrocarbonate (DEPC)-treated water and the mixture was heated to 65° C. for 10 minutes. After chilling the mixture on ice, the reaction components were added so that the final composition was approximately 20 mM Tris-HCl (pH 8.4), 50 mM KCl, 2.5 mM $MgCl_2$, 100 $\mu g/ml$ bovine serum albumin, 500 nM AP, 500 $\mu M$ each of dATP, dCTP, dGTP, and dTTP, and 50 ng/$\mu l$ RNA in a volume of 19 $\mu l$. The reaction mixture was heated to 42° C. and 1 $\mu l$ (20 units) of SuperScript reverse transcriptase was added. After incubation for 30 minutes at 42° C., the reaction mixture was chilled on ice and 1 $\mu l$ RNaseH 12 units) was added. RNaseH digestion was conducted for 10 minutes at a temperature of 42° C. The reaction mixture was stored at −20° C. prior to the PCR.

For PCR, four identical 40 $\mu l$ mixtures were prepared each with the following composition: 1 $\mu l$ of uterus poly $A^+$ cDNA in 40 mM KCl, 70 mM Tris-HCl (pH 8.8), 0.1% Triton X-100, 1 mM $MgCl_2$, 0.25 $\mu M$ CKCB1, and 0.5 $\mu M$ AP. Reagents from the 3' RACE system were not used for PCR. Both the CKCB1 and AP primers were synthesized on an Applied Biosystems, Inc. model 392 oligonucleotide synthesizer. After deprotection, lyophilization, and resuspension in DEPC-treated water the optical density of each solution was measured at a wavelength of 260 nm. Based on the optical density measurements, a 10 $\mu M$ solution of each oligonucleotide was prepared in DEPC-treated water. The crude oligonucleotide solutions were used for PCR with no further purification. The concentration of crude AP that produced identical results to the AP supplied with the 3' RACE system was experimentally determined; 0.4 $\mu M$ crude AP was equivalent to 0.2 $\mu M$ AP from Life Technologies, Inc. in the PCR.

The 40 $\mu l$ PCR reactions were heated to 94° C. in a temperature cycler before adding to each a 10 $\mu l$ mixture containing the following: 1.25 units AmpliTaq DNA polymerase (Perkin Elmer Cetus, Norwalk, Conn.), 40 mM KCL, 70 mM Tris-HCl, pH 8.8), 0.1% Triton-X-100, 1 mM $MgCl_2$, and 1 mM each of dATP, dTTP, dGTP, and dCTP. The final concentration of each reagent in the PCR was approximately 1 $\mu l$ uterus cDNA per 50 $\mu l$, 1.25 units AmpliTaq DNA polymerase per 50 $\mu l$, 40 mM KCl, 70 mM Tris-HCl (pH 8.8). 0.1% Triton X-100, 1 mM $MgCl_2$, 0.2 $\mu M$ CKCB1, 0.4 $\mu M$ AP, and 0.2 mM each of dATP, dTTP, dGTP, and dCTP. After completing a 5 minute incubation at 94° C., a "Touchdown" PCR temperature cycling program was performed according to Don, R. H., Cox P. T., Wainwright. B. J., Baker, K. and Mattick, J. S. (1991) Nucl. Acids Res. 19, 4008, by varying the annealing temperature from 73° C. to 63° C.

After PCR amplification, the four reactions were combined and the DNA products were size-fractionated by electrophoresis on a 5% polyacrylamide gel. A DNA product of aproximately 450 bp was excised from the gel and purified by electroelution in dialysis tubing. The eluate was extracted with a 50:50 (v:v) mixture of phenol and chloroform, ethanol precipitated, dried, and resuspended in 10 $\mu l$ sterile water.

Due to the template independent terminal transferase activity of Taq DNA polymerase and its strong preference for dATP (Clark, J. M. (1988) Nucl. Acids Res. 16, 9677 and Mole. S. E., Iggo, R. D. and Lane D. P. (1989) Nucl. Acids Res. 17, 3319), the purified 450 bp PCR fragment was expected to have a single deoxyadenosine residue at each 3' end. For subcloning and characterizing the PCR fragment, a pBluescriptSK+ (Stratagene, La Jolla. Calif) "T-vector" was prepared essentially as described by Marchuk et al. (1991) Nucl. Acids Res. 19, 1154. The pBluescript plasmid (20 $\mu g$) was digested with EcoRV restriction endonuclease and then purified by extraction with a 50:50 (v:v) mixture of phenol and chloroform. After ethanol precipitation, the DNA was treated with 9 units of Taq DNA polymerase for 2 hours at 70° C. in a 50 $\mu l$ reaction containing 50 mM KCl, 10 mM Tris-HCl (pH 9.0), 0.1% Triton X-100, 1.5 mM $MgCl_2$, and 2 mM dTTP. The vector was again purified by extraction with phenol and chloroform (50:50 v:v) and ethanol precipitation. This procedure resulted in the addition of a single deoxythymidine residue to each 3 ' terminus, and rendered the vector compatible for insertion of DNA fragments synthetized with Taq DNA polymerase.

The unphosphorylated 450 bp PCR fragment was inserted into the T-vector in a reaction with T4 DNA ligase (New England Biolabs, Beverly, Mass.) using the conditions recommended by the manufacturer. The ligation reaction was incubated for approximately 72 hours at 16° C. and then used to transform competent E. coli XL1-Blue cells (Stratagene, La Jolla, Calif.). The transformed cells were plated onto LB agar containing 50 μg/ml ampicillin. Prior to plating the cells, 100 μl 2% X-gal (Life Technologies, Inc., Grand Island, N.Y.) and 40 μl 100 mM IPTG (Life Technologies, Inc., Grand Island, N.Y.) were sequentially spread onto the agar surface of each plate and allowed to dry. After an overnight incubation at 37° C., colonies with blue pigment and unpigmented colonies (white) were visible. Plasmid DNA was purified from cultures of 12 white colonies. All 12 isolates contained the 450 bp insert. Five clones were chosen for further analysis: 3CB4, 3CB6, 3CB7, 3CB8 and 3CB9. DNA sequence analysis was done using a Sequenase version 2.0 kit (United States Biochemical, Cleveland, Ohio).

5' RACE cloning procedure

The 5' RACE system for Rapid Amplification of cDNA ends was purchased from Life Technologies, Inc.. Grand Island, N.Y. Human uterus poly $A^+$ RNA was purchased from Clontech Laboratories, Palo Alto, Calif. The 5' RACE cloning experiments were done using the protocol and reagents supplied with the 5' RACE system with the following exceptions: (a) the CKCB7, ACP and UAP primers were synthetized on an Applied Biosystem, Inc. model 392 oligonucleotide synthetizer and prepared as described for 3' RACE cloning, and (b) the "Touchdown" PCR temperature cycling program described for 3' RACE cloning was used for cDNA amplification. First strand cDNA was synthetized as follows: 1 μl (1 μg) of uterus poly $A^+$ RNA was comnbined with 0.5 μl of a 10 μM solution of CKCB7 and 13.5 μl of DEPC-treated water and the mixture was heated at 70° C. for 10 minutes. After chilling the mixture on ice, the reaction components were added so that the final composition was approximately 20 nM Tris-HCl (pH 8.4), 50 mM KCl, 3 mM $MgCl_2$, 10 mM DTT, 200 mM CKCB7, 400 μM each of dATP, dCTP, dGTP, and dTTP, and 40 ng/μl RNA in a volume of 24 μl. The reaction mixture was heated to 42° C. and 1 μl (220 units) of Superscript II reverse transcriptase was added. After incubation for 30 minutes at 42° C. and for 15 minutes at 70° C., the reaction mixture was placed at 55° C. and 1 μl RNaseH (2 units) was added. RNaseH digestion was conducted for 10 minutes at a temperature of 55° C.

The cDNA was separated from unincorporated dNTPs, CKCB7, and proteins unsing a Glassmax DNA Isolation Spin Cartridge (included in the 5' RACE system). Specifically, 120 μl of binding solution (6M NaI) was added to the first strard reaction, and the CDNA/NaI solution was transferred to a GLASSMAX spin cartridge. Following centrifugation at 13,000× g for 20 seconds, 0.4 ml of cold (4° C.) 1× wash buffer was added. The spin cartridge was centrifuged at 13,000× g for another 20 seconds. This step was repeated two additional times. After washing twice with 400 μl of cold (4° C.) 70% ethanol, the cDNA was eluted by adding 50 μl of sterilized, distilled water to the spin cartridge and centrifuging at 13000× g for 20 seconds. A homopolymer tail was added to the 3' end of the cDNA using terminal deoxynucleotidyl transferase (TdT) and dCTP. The tailing reaction was performed in a PCR compatible buffer. 10 μl of purified cDNA was combined with 7.5 μl of DEPC-treated water, 2.5 μl of 10× reaction buffer, 1.5 μl of a 25 mM solution of MgCl 2 and 2.5 μl of a 2 mM solution of dCTP. The reaction mixture was incubated for 2 to 3 minutes at 94° C. After chilling for 1 minute on ice, 1 μl of TdT (10 units/μl) was added. The final composition was therefore: 10 μl cDNA in 20 mM Tris-HCl (pH 8.4), 50 mM KCl, 1.5 mM $MgCl_2$, 200 μM dCTP, 0.4 units/μl TdT. The reaction mixture was incubated for 10 minutes at 37° C. and then for 10 minutes at 70° C. to inactivate the TdT.

For the PCR, four different reactions were prepared with the following final primer concentrations (per 50 μl):

1. 400 nM ACP
2. 800 nM ACP
3. 360 nM UAP and 40 nM ACP (UAP:ACP, 9:1)
4. 720 nM UAP and 80 nM ACP (UAP:ACP, 9:1)

The final concentrations (per 50 μl) of the remaining components in all four reactions were identical: 5 μl of uterus poly $A^+$ dC-tailed cDNA in 20 mM Tris-HCl (pH 8.4), 50 mM KCl, 1.5 mM $MgCl_2$, 400 nM CKCB2, and 200 μM each dATP, dCTP, dGTP and dTTP. The components, including the ACP and UAP primers, were mixed in an initial volume of 45 μl and heated to 94° C. in a temperature cycler. A 5 μl mixture of 1.25 units of AmpliTaq DNA polymerase (Perkin Elmer Cetus, Norwalk, Conn.) in 20 mM Tris-HCl (pH 8.4) was then added to each reaction to bring the final volume to 50 μl. The "Touchdown" PCR temperature cycling program (as described for 3' RACE cloning) was used to amplify 5' cDNA fragment.

After PCR amplification, the four reactions were combined and the DNA products were size-fractionated by electrophoresis on an 8% polyacrylamide gel. A DNA product of approximately 230 bp was excised from the gel, purified, and subcloned into the "T-vector" as described for the 450 bp 31 RACE fragment. Five clones were chosen for further analysis: 5CB2, 5CB3, 5CB5, 5CB6, 5CB11. DNA sequence analysis was done using a Sequenase version 2.0 kit (United States Biochemical. Cleveland, Ohio).

FIG. 8 reports the complete Component B cDNA sequence assembled from RACE clones 5CB3 and 3CB7, in which the restriction sites are indicated.

By sequence alignment the cDNA sequence of clones 5cb3, 5cb6, 5cb11 and 3cb4, 3cb7, 3cb9 were shown to perfectly match with the Component B exons (genomic clone 4D of Example 3). Although the present invention was illustrated with specific examples, it is clear that modifications can be performed on the operations as described always remaining within the spirit and scope of the invention.

LEGENDS TO FIGURES

FIG. 1. Flow chart of the process of purification of Component B from urine.

FIG. 2. Restriction map of Component B genomic transcriptional unit (such Component B genomic DNA reported in SEQ ID NO: 2 with the amino acid sequence of the encoded protein present as SEQ ID NO: 4). Arrows indicate the splicing sites.

FIG. 3. Sequence of Component B promoter region (said Component B promoter region reported in SEQ ID NO: 2). Binding sites for AP-1, AP-2, Sp-1 and E-boxes transcription factors are indicated. TATA box is indicated. GRE is also indicated.

FIG. 4. Restriction map of Component B gene. The derived mRNA is shown below the genomic gene by a line, the boxed region represents the protein encoding sequence.

FIG. 5. Restriction map of clone 4D insert.

FIG. 6. Restriction map of pBSCB4D plasmid.

FIG. 7. General strategy used for RACE cloning of Component B DNA sequence.

FIG. 8. Complete Component B cDNA sequence, in which the restriction sites are indicated (said Component B cDNA reported in SEQ ID NO: 3).

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
        (A) LENGTH: 81 amino acids
        (B) TYPE: amino acid
        (D) TOPOLOGY: linear (ii) MOLECULE TYPE: protein (iii) HYPOTHETICAL: NO (iii) ANTI-SENSE: NO (vi) ORIGINAL SOURCE:
      (A) ORGANISM: URINE (xi) SEQUENCE DESCRIPTION: SEQ ID NO: 1:

```
Leu Lys Cys Tyr Thr Cys Lys Glu Pro Met Thr Ser Ala Ser Cys Arg
 1               5                  10                  15

Thr Ile Thr Arg Cys Lys Pro Glu Asp Thr Ala Cys Met Thr Thr Leu
            20                  25                  30

Val Thr Val Glu Ala Glu Tyr Pro Phe Asn Gln Ser Pro Val Val Thr
        35                  40                  45

Arg Ser Cys Ser Ser Ser Cys Val Ala Thr Asp Pro Asp Ser Ile Gly
    50                  55                  60

Ala Ala His Leu Ile Phe Cys Cys Phe Arg Asp Leu Cys Asn Ser Glu
65                  70                  75                  80

Leu
```

(2) INFORMATION FOR SEQ ID NO: 2:

(i) SEQUENCE CHARACTERISTICS:
        (A) LENGTH: 2031 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (ix) FEATURE:
      (A) NAME/KEY: CDS
      (B) LOCATION: join(578..635, 1041..1160, 1687..1817)

(ix) FEATURE:
      (A) NAME/KEY: exon
      (B) LOCATION: join(552..635, 1041..1160, 1687..2012)

(ix) FEATURE:
      (A) NAME/KEY: mat_peptide
      (B) LOCATION: join(1049..1159, 1686..1817)

(ix) FEATURE:
      (A) NAME/KEY: TATA_signal
      (B) LOCATION: join(524..529, 1992..1998)

(ix) FEATURE:
      (A) NAME/KEY: GC_signal
      (B) LOCATION: 493..498
      (D) OTHER INFORMATION: /note= "GC-rich box represents the
          binding site for the transcription factor Sp-1"

```
    (ix) FEATURE:
         (A) NAME/KEY: promoter
         (B) LOCATION: 1..551

(ix) FEATURE:
         (A) NAME/KEY: misc_feature
         (B) LOCATION: join(17..22, 24..29, 55..60, 66..71, 434..439)
         (D) OTHER INFORMATION: /standard_name= "E-box"
             /note= "E-box site is described in R.E. Kingston
             Current Opinion Cell. Biol., 1989, Vol.1,
             1081-1087 (Citation 1) "

(ix) FEATURE:
         (A) NAME/KEY: misc_signal
         (B) LOCATION: 329..342
         (D) OTHER INFORMATION: /function= "Glucocorticoid
             responsive element"
             /standard_name= "GRE"

(ix) FEATURE:
         (A) NAME/KEY: protein_bind
         (B) LOCATION: 469..475
         (D) OTHER INFORMATION: /standard_name= "AP-1 site"
             /note= "AP-1 site is the binding site for the
             transcription factor AP-1"

(ix) FEATURE:
         (A) NAME/KEY: protein_bind
         (B) LOCATION: 191..197
         (D) OTHER INFORMATION: /standard_name= "AP-2 site"
             /note= "AP-2 site is the binding site for the
             transcription factor AP-2"

(ix) FEATURE:
         (A) NAME/KEY: misc_signal
         (B) LOCATION: join(578..634, 1040..1049)
         (D) OTHER INFORMATION: /function= "Putative signal
             peptide"

(ix) FEATURE:
         (A) NAME/KEY: intron
         (B) LOCATION: join(636..1040, 1161..1686, 2013..2031)

(xi) SEQUENCE DESCRIPTION: SEQ ID NO: 2:

TGGCCCATGC TACCCTCACC TGACACCTGC TTCCTACCTC TGGTTTCTAC TTTGCAGGTG      60

TGTATCAGGT GTACACAGAC CAGGTAGAGG TCTGTGGAGA GGGCTGCAGG CCAGGCTGCA     120

GGGAAGGGGT GCCAGGCGGG GCTAGAGCAA CAAGGGCAGA GGCTACACTG AACCTGGGTC     180

YTAAGGGTCC CCCAGGCTGG GGCTGGGTGG CCTATGTGAA CCCCAGAGGC ACAGCCAGGA     240

CATGGGGGCT CATCAGAGGG GCAGTCTGAG CTCAGCAGGA AAGGCCTTCT CTGTCAGAGC     300

TGTCCCAGGA CCACTGGACA TGGCTGAGGA ACAGTGAGTT CCCCAGTGTT GGAGGTGTGC     360

AAGCAGAGGC CTGGCCATCG TCCTCAGACA CAGCTCCCAG ATCCAGCTCC CTGCCCGTCT     420

GCCATGTTCC TGCCAGCTGC CTCCCCACTG GGCCCTTTAC CACGTTCCTG ACTCACACGG     480

CCGGTTCTGC CACCGCCCAG AAGCCGGTGC CAAGGGCCT  GGCTATAAAT CCTTGATGTG     540

AGGCTGGCTA CCTCTCATCA CTTCTGAGCA CGGAGCA ATG GCC TCT CGC TGG GCT      595
                                        Met Ala Ser Arg Trp Ala
                                        -22         -20

GTG CAG CTG CTG CTC GTG GCA GCC TGG AGC ATG GGC TGT  G GTGAGTGGGC     645
Val Gln Leu Leu Leu Val Ala Ala Trp Ser Met Gly Cys
    -15                 -10                 -5

CGCAGGCTGG TGGGGACCTT GCCTCTGAGC TTGTCTGCCC ACCTCCTAGG GGATGGGGC      705

TGTTGGGGGT GCTTTGTGGC TGAGAGCCTC CTTAGGCCTC CATGAGGCTC ACCCTCCTCA     765

TTCTCAGTGA GCCTCCTGGG TCCCAGAGCC CAGCTTCACC CTGGGACAGG GGTCACGGCT     825

CCACTCTGCA GGAAGGGAGA CTGAGGCTTG GTGGAGGGAT GCAGCATTCA AGTCTGTGGC     885

TCAGCTCAGT TAGAGAAAGC TGCCAGAGAG GCCCCTTGAA GGSCTGCCCG GGGCCTTGAA     945
```

```
AGATGTCAGC GAGACTCCTT CAGCCCCTGC CTCCTGGTTC CAGGATGAGV CCACCGAGGT    1005

CAGGTGATGA GGTTCTGCCC CCATCCCTCA CCCAG GT GAG GCC CTC AAG TGC        1057
                                       Gly Glu Ala Leu Lys Cys
                                            -2           1

TAC ACC TGC AAG GAG CCC ATG ACC AGT GCT TCC TGC AGG ACC ATT ACC      1105
Tyr Thr Cys Lys Glu Pro Met Thr Ser Ala Ser Cys Arg Thr Ile Thr
         5                  10              15

CGC TGC AAG CCA GAG GAC ACA GCC TGC ATG ACC ACG CTG GTG ACG GTG      1153
Arg Cys Lys Pro Glu Asp Thr Ala Cys Met Thr Thr Leu Val Thr Val
 20              25              30              35

GAG GCA  G GTGAGGCCAG GCCCCACGGC AGCCCTGGGT GCAGTGGAGT CAGGGCCACC    1210
Glu Ala

TCCCCCAAGT GCGTCCCTCC TTTGCTGGTG CTCCTCCCGG CCCAAAAGGA AGCAGGTGGG    1270

ATGGGCAGAA CAGGCTGCCA CACCTTGGCA GGGGTGCCTT CCACGAGGGT GGCACAGCCC    1330

CCTCAGAGAC CCAGTCCTGG GGCACCAGGC GCTGGAGGTG GGTGGGGCTT AATGGCCGGG    1390

GTACCCTGGG GGGCTCAAAC CCCAGCTCTG ACACAGACCC ACTGGGTGGT GTTGCCACAG    1450

CCTCTGGGCT CGGGCTCCCA TCTCAGCGCA GGCACTTCAG AGGTCTGACA AGGCCTAATA    1510

ATTCATGAAC AGGTCACAGT CAGAGGAGGG CTGGGCCCTG GGTGGCTTCA CAGATGTGGA    1570

CTATTGGGAA CAGGGATCAC AGGGAGGKTG AGGTCAGSCG ACGGCGGCTG GGAGCAGTGC    1630

AGCAGCAGGC AGGCGCTGCA GGGGAGTGAG GGTTCTGACA CTGGCCCACC CTGCAG  AG    1688
                                                                Glu

TAC CCC TTC AAC CAG AGC CCC GTG GTG ACC CGC TCC TGC TCC AGC TCC      1736
Tyr Pro Phe Asn Gln Ser Pro Val Val Thr Arg Ser Cys Ser Ser Ser
         40              45              50

TGT GTG GCC ACC GAC CCC GAC AGC ATC GGG GCC GCC CAC CTG ATC TTC      1784
Cys Val Ala Thr Asp Pro Asp Ser Ile Gly Ala Ala His Leu Ile Phe
 55              60              65              70

TGC TGC TTC CGA GAC CTC TGC AAC TCG GAA CTC TGAACCCAGG GCGGCAGGGC    1837
Cys Cys Phe Arg Asp Leu Cys Asn Ser Glu Leu
             75              80

GGAAGGTGCT CCTCAGGCAC CTCCTCTCTG ACGGGGCCTG GCTCCACCTG TGATCACCTC    1897

CCCCTGCTTC CTGCTGCTGT GGCACAGCTC ACTCATGGGG TCTGAGGGGA GAGAAGCACA    1957

CCAGGGGCGC CCTCTGCCTT CCATACCCCA CGCTTATAAA ACATAACTAA GCCAAGAGTG    2017

GACATGACTT TTGT                                                      2031
```

(2) INFORMATION FOR SEQ ID NO: 3:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iii) ANTI-SENSE: NO (ix) FEATURE:
        (A) NAME/KEY: CDS
        (B) LOCATION: 22..330

(ix) FEATURE:
        (A) NAME/KEY: mat_peptide
        (B) LOCATION: 88..330

(ix) FEATURE:

(A) NAME/KEY: TATA_signal
            (B) LOCATION: 505..511

(xi) SEQUENCE DESCRIPTION: SEQ ID NO: 3:

ATCACTTCTG AGCACGGAGC A ATG GCC TCT CGC TGG GCT GTG CAG CTG CTG                51
                       Met Ala Ser Arg Trp Ala Val Gln Leu Leu
                       -22     -20                 -15

CTC GTG GCA GCC TGG AGC ATG GGC TGT GGT GAG GCC CTC AAG TGC TAC                99
Leu Val Ala Ala Trp Ser Met Gly Cys Gly Glu Ala Leu Lys Cys Tyr
        -10                 -5                   1

ACC TGC AAG GAG CCC ATG ACC AGT GCT TCC TGC AGG ACC ATT ACC CGC                147
Thr Cys Lys Glu Pro Met Thr Ser Ala Ser Cys Arg Thr Ile Thr Arg
 5           10                  15                  20

TGC AAG CCA GAG GAC ACA GCC TGC ATG ACC ACG CTG GTG ACG GTG GAG                195
Cys Lys Pro Glu Asp Thr Ala Cys Met Thr Thr Leu Val Thr Val Glu
             25                  30                  35

GCA GAG TAC CCC TTC AAC CAG AGC CCC GTG GTG ACC CGC TCC TGC TCC                243
Ala Glu Tyr Pro Phe Asn Gln Ser Pro Val Val Thr Arg Ser Cys Ser
                 40                  45                  50

AGC TCC TGT GTG GCC ACC GAC CCC GAC AGC ATC GGG GCC GCC CAC CTG                291
Ser Ser Cys Val Ala Thr Asp Pro Asp Ser Ile Gly Ala Ala His Leu
             55                  60                  65

ATC TTC TGC TGC TTC CGA GAC CTC TGC AAC TCG GAA CTC TGAACCCAGG                 340
Ile Phe Cys Cys Phe Arg Asp Leu Cys Asn Ser Glu Leu
         70                  75                  80

GCGGCAGGGC GGAAGGTGCT CCTCAGGCAC CTCCTCTCTG ACGGGGCCTG GCTCCACCTG              400

TGATCACCTC CCCCTGCTTC CTGCTGCTGT GGCACAGCTC ACTCATGGGG TCTGAGGGGA              460

GAGAAGCACA CCAGGGGCGC CCTCTGCCTT CCATACCCCA CGCTTATAAA ACATAACTAA              520

GCCAAAAAAA AAAAAAAAA                                                          540

(2) INFORMATION FOR SEQ ID NO: 4:

(i) SEQUENCE CHARACTERISTICS:
        (A) LENGTH: 103 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Ser Arg Trp Ala Val Gln Leu Leu Val Ala Ala Trp Ser
-22     -20                 -15                 -10

Met Gly Cys Gly Glu Ala Leu Lys Cys Tyr Thr Cys Lys Glu Pro Met
    -5                   1                   5                  10

Thr Ser Ala Ser Cys Arg Thr Ile Thr Arg Cys Lys Pro Glu Asp Thr
                15                  20                  25

Ala Cys Met Thr Thr Leu Val Thr Val Glu Ala Glu Tyr Pro Phe Asn
             30                  35                  40

Gln Ser Pro Val Val Thr Arg Ser Cys Ser Ser Ser Cys Val Ala Thr
             45                  50                  55

Asp Pro Asp Ser Ile Gly Ala Ala His Leu Ile Phe Cys Cys Phe Arg
     60                  65                  70

Asp Leu Cys Asn Ser Glu Leu
75                  80

(2) INFORMATION FOR SEQ ID NO: 5:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 5:

TGACTCACAC GGCCGGTTCT                                           20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 6:

CAGCCATGTC CAGTGGTCCT                                           20

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 7:

ACCACAGCCC ATGCTCCA                                             18

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 8:

TGCAGGAAGC ACTGGTCAT                                            19

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 9:

TCTGGCTTGC AGCGGGTAAT GGT                                                          23

(2) INFORMATION FOR SEQ ID NO: 10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 10:

ATGACCAGTG CTTCCTGC                                                                18

(2) INFORMATION FOR SEQ ID NO: 11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 11:

ATCCCACCTG CTGCCTTTTG                                                              20

(2) INFORMATION FOR SEQ ID NO: 12:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 12:

CGGCGGCTGG GAGCAGT                                                                 17

(2) INFORMATION FOR SEQ ID NO: 13:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 13:

ATGGAATTCT AYCCATTYAA YCARTC                                                    26

(2) INFORMATION FOR SEQ ID NO: 14:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 14:

ATGGAATTCT AYCCATTYAA YCARAG                                                    26

(2) INFORMATION FOR SEQ ID NO: 15:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 15:

GTAGAATTCG CGCCAATGGA RTCNGGRTC                                                 29

(2) INFORMATION FOR SEQ ID NO: 16:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 16:

GTAGAATTCG CGCCAATGCT RTCNGGRTC                                                 29

(2) INFORMATION FOR SEQ ID NO: 17:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 17:

AGTACCCCTT CAACCAGAG                                                            19

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 18:

CAGACACCAT GAGTGAGCTG                                      20

(2) INFORMATION FOR SEQ ID NO: 19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 19:

GACACCTCCT CTGTGACGG                                       19

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 20:

CCAGTTCTGT AGGGTGTCAG T                                  21

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 21:

TCAAGTGCTA CACCTGCAAG GAG                                23

(2) INFORMATION FOR SEQ ID NO: 22:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 22:

CGTCAGAGAG GAGGTG                                                    16

(2) INFORMATION FOR SEQ ID NO: 23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 23:

ACCGTCACCA GCGTGGTC                                                  18

(2) INFORMATION FOR SEQ ID NO: 24:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 24:

GGCCACGCGT CGACTAGTAC TTTTTTTTTT TTTTTTT                              37

(2) INFORMATION FOR SEQ ID NO: 25:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (ix) FEATURE:
        (A) NAME/KEY: modified_base
        (B) LOCATION: join(36..37, 41..42, 46..47)
        (D) OTHER INFORMATION: /mod_base= i (xi) SEQUENCE DESCRIPTION: SEQ ID NO: 25:

CTACTACTAC TAGGCCACGC GTCGACTAGT ACGGGNNGGG NNGGGNNG                  48

(2) INFORMATION FOR SEQ ID NO: 26:

```
    (i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iii) ANTI-SENSE: NO (xi) SEQUENCE DESCRIPTION: SEQ ID NO: 26:

CTACTACTAC TAGGCCACGC GTCGACTAGT AC                                    32
```

I claim:

1. An isolated and purified polypeptide comprising the peptide sequence of SEQ ID NO:1 or its salts and functional derivatives selected from the group consisting of N-terminal or C-terminal acyl derivatives, or mixtures thereof.

2. A process for the production of the polypeptide according to claim 1 comprising the following steps:

a) adsorption of urine, at pH acid, on kaolin and extraction with ammonia
   b) elution of fraction (a) on Bio Rex 70 resin with ammonia
   c) elution of fraction (b) on DEAE Sepharose resin with acetate buffer
   d) elution of fraction (c) on CM Sepharose resin with acetate buffer
   e) elution of fraction (d) on HPLC C18 resin with a mixture of acetate buffer and acetonitrile
   f) elution of fraction (e) on DE-52 resin with acetate buffer
   g) elution of fraction (f) on D-Zephyr resin with acetate buffer
   h) elution of fraction (g) on HPLC C18 resin with a mixture of aqueous trifluoroacetic acid and acetonitrile
   i) elution of fraction (h) on D-Zephyr resin with acetate buffer.

3. A process according to claim 2 wherein the urine is human urine.

4. An isolate DNA molecule comprising the DNA sequence coding for the polypeptide according to claim 1.

5. An isolated DNA molecule which hybridizes with the DNA molecule according to claim 4, wherein said hybridization is conducted with a horseradish peroxidase oligoprobe and hybridized plaques formed are detected by enhanced chemiluminescence reagents under stringent hybridization conditions wherein said stringent hybridization conditions comprise 5×SSC, 0.02% SDS, 0.1% N-laurylsarcosine at 42° C.

6. An isolated DNA molecule comprising the nucleotide sequence of SEQ ID NO: 2.

7. An isolated cDNA molecule comprising the nucleotide sequence of SEQ ID NO: 3.

8. An expression vector comprising the DNA molecule according to claim 4.

9. A host cell transformed with an expression vector according to claim 8.

10. An essentially pure protein, comprising the amino acid sequence shown in SEQ ID NO:1, or its salts, obtainable through a process comprising the following steps:

a) adsorption of urine, at pH acid, on kaolin and extraction with ammonia
   b) elution of fraction (a) on ion exchange resin with ammonia
   c) elution of fraction (b) on ion exchange resin with acetate buffer
   d) elution of fraction (c) on ion exchange resin with acetate buffer
   e) elution of fraction (d) on ion exchange resin with a mixture of acetate buffer and acetonitrile
   f) elution of fraction (e) ion exchange resin with acetate buffer
   g) elution of fraction (f) on ion exchange resin with acetate buffer
   h) elution of fraction (g) on ion exchange resin with a mixture of aqueous trifluoroacetic acid acetonitrile
   i) elution of fraction (h) on ion exchange resin with acetate buffer.

11. A pharmaceutical composition comprising the protein according to claim 10, or its salts, or mixtures thereof in combination with one or more pharmaceutically acceptable eccipients or eluents.

12. A composition comprising an effective amount of the polypeptide according to claim 1 to inhibit the binding of TGF-alpha to its receptor and a pharmaceutically acceptable carrier.

13. An isolated and purified polypeptide according to claim 1 wherein said polypeptide is sulfated at position Tyr(39).

14. The isolated DNA molecule according to claim 5, wherein said hybridization conditions comprise hybridization at 42° C. for 45 minutes.

15. The isolated DNA molecule according to claim 5, wherein said hybridization conditions comprise hybridization at 50° C.

* * * * *